United States Patent [19]

Leston

[11] 4,009,212

[45] Feb. 22, 1977

[54] METHOD FOR THE PREPARATION OF META DIHYDROXYBENZENES

[75] Inventor: Gerd Leston, Pittsburgh, Pa.

[73] Assignee: Koppers Company, Inc., Pittsburgh, Pa.

[22] Filed: Aug. 7, 1975

[21] Appl. No.: 602,767

Related U.S. Application Data

[63] Continuation-in-part of Ser. No. 334,270, Feb. 21, 1973, abandoned.

[52] U.S. Cl. .......................... 260/628; 260/621 R; 260/625
[51] Int. Cl.² ........................................ C07C 37/04
[58] Field of Search ............... 260/628, 621 R, 625

[56] References Cited

UNITED STATES PATENTS

| | | | |
|---|---|---|---|
| 2,225,564 | 12/1940 | Maistre | 260/628 |
| 2,407,044 | 9/1946 | Tyrer | 260/628 |

FOREIGN PATENTS OR APPLICATIONS

| | | | |
|---|---|---|---|
| 649,945 | 2/1951 | United Kingdom | 260/628 |

*Primary Examiner*—James O. Thomas, Jr.
*Assistant Examiner*—W. B. Lone
*Attorney, Agent, or Firm*—Robert D. Yeager; Olin E. Williams

[57] ABSTRACT

A process for the preparation of dihydroxybenzenes whereby there are obtained primarily meta isomers of the dihydroxybenzenes includes the steps of: preparing a mixture of sulfonic acid isomers by sulfonation-isomerization of an hydroxybenzene having the formula:

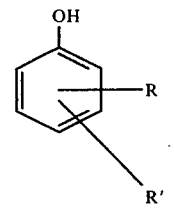

in which R and R' are selected from the group consisting of hydrogen and an alkyl radical having at most 4 carbon atoms per molecule, the total carbon atoms in radicals R and R' being at most 4; subjecting the so-produced sulfonic acids to selective hydrolyzation in aqueous medium at a temperature between about 100° and 150° C., the monohydroxy benzene being recovered by the said selective hydrolyzation in an enriched concentration that makes it readily recoverable by recycle in the process or other separation methods, and unhydrolyzed sulfonic acid remaining in the said aqueous medium; caustically fusing the said unhydrolyzed sulfonic acid, and liberating by acidification the desired dihydroxybenzene.

5 Claims, No Drawings

METHOD FOR THE PREPARATION OF META DIHYDROXYBENZENES

CROSS REFERENCE TO RELATED APPLICATIONS

This application is a continuation in part of application Ser. No. 334,270, filed Feb. 21, 1973, now abandoned.

BACKGROUND OF THE INVENTION

1. Field of the Invention

This invention relates to a process for the preparation of selected isomers of dihydroxybenzenes.

2. Description of the Prior Art

It is well known that phenols can be prepared by sulfonation of benzene to produce a sulfonic acid which is thereafter converted by caustic fusion to the phenolate, the phenol being liberated by treatment with acid, acid gases, or the like. A process of producing polyhydroxy aromatic compounds by a process of dry fusion of an alkali metal aromatic poly sulfonate with an alkali metal hydroxide is disclosed and claimed in Webb U.S. Pat. No. 2,736,754. In such processes resorcinol is produced when the sulfonate is sodium m-benzenedisulfonate (cf. Noller, *Textbook of Organic Chemistry*, 2nd Edition, p. 394). Other processes, referred to in my copending application Ser. No. 602,768 filed Aug. 7, 1975, also a continuation-in-part of my application Ser. No. 334,270, filed Feb. 21, 1973, now abandoned disclose the controlled sulfonation-isomerization of alkyl aromatics to produce, upon caustic fusion of the resulting sulfonates, mixtures of isomers of alkylhydroxyaromatics.

SUMMARY OF THE INVENTION

Generally, the process of the present invention comprises a sulfonation-isomerization at a temperature between about 130° and 200° C of hydroxybenzene or an alkylhydroxybenzene having the formula hereinabove defined to produce a mixture of isomerized hydroxybenzenesulfonic acids including alkyl hydroxybenzenesulfonic acids. This mixture is then selectively hydrolyzed by treatment in aqueous medium at temperatures between about 100° and 150° C to produce either hydroxybenzene (phenol), if that is the feed stock, or at least one hydrolyzed isomer of a hydroxyalkylbenzene which is recoverable as an hydrolyzed isomer in enriched relative concentration.

Thereafter the unhydrolyzed hydroxybenzenesulfonic acid remaining in the aqueous medium is neutralized with an alkaline reactant to form the corresponding sulfonate, is dried, fused with caustic, the dried cake is taken up in aqueous solution, and the solution acidified to liberate the meta-dihydroxybenzene isomer.

DETAILED DESCRIPTION OF THE INVENTION

Hydroxybenzenes that are suitable for employment in the present process include phenol, o-, m-, and p-cresol, various xylenols, o-, m-, and p-ethylphenol, o-, m-, and p-n-propylphenol, o-, m-, and p-hydroxycumene, carvacrol, (2-methyl-5-isopropylphenol), and thymol (2-isopropyl-5-methylphenol).

The meta isomers of certain of the foregoing phenol derivatives, e.g., meta cresol, can be obtained for use in this process by employment of the process of my aforementioned copending application. Even though, however, the cresol isomer, for example, can thereby be provided in purity of as high as 98 percent, the sulfonation-isomerization of these compounds will again result in an isomeric mixture calling for the selective hydrolyzation process of this invention to provide the ultimate, desired dihydroxy phenol. Hydroxybenzenes having longer or more complex alkyl radicals than those above-named are themselves rarely available and introduce the obstacle of steric hindrance to the recovery of practicable yields of dihydroxy alkyl phenols. Generically expressed, therefore, hydroxybenzenes suitable for use in the present process are those having the formula:

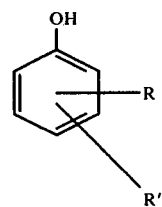

in which R and R' are selected from the group consisting of hydrogen and an alkyl radical having at most 4 carbon atoms per molecule, the total carbon atoms in radicals R and R' being at most four.

Sulfonation and isomerization can take place as a single step or in two steps if separate isomerization is to be effected. Because of the strong activating effect of the hydroxy group, sulfonation takes place very readily. For example, sulfonation of phenol at room temperature by concentrated sulfuric acid yields chiefly the ortho isomer, whereas at 100° C. the para isomer, p-phenolsulfonic acid, predominates. As the present process, when phenol is employed, is directed toward ultimate recovery of the m-dihydroxybenzene, resorcinol, isomerization is performed in such manner as to provide mixtures of isomers wherein the meta sulfonic acid is present in substantial amount. The selective hydrolyzation step of this invention is preferably applied to isomer mixtures of sulfonic acids in which a substantial quantity of the more difficulty hydrolyzable isomer is present. Thus, a preferred feedstock is inherently produced when the alkyl hydroxybenzene is the product of the process of the said copending application, because, while, as aforementioned sulfonation will effect some isomerization, sulfonation of alkyl hydroxybenzenes can be performed at lower temperature that that of alkylbenzenes and more of the original isomeric distribution can thus be preserved.

The isomeric mixture of sulfonic acids then undergoes preferential hydrolyzation by the addition of water, preferably of steam at temperatures between about 100° and 150° C. Lower temperatures, as the specific example herein demonstrates, fail to effect hydrolysis of the alkyl hydroxybenzenesulfonic acid, and higher temperatures result in the formation of oxidation products, e.g. resorcylic acid. Hydrolysis is preferably carried out at atmospheric pressure and the amount of water utilized is controlled so as to maintain a proper temperature of reaction. If too much water is used, the hydrolysis temperature of the various sulfonic acids will not be maintained.

The alkylhydroxybenzene recovered during the selective hydrolyzation can either be reused as additional feedstock or used to enrich the starting materials. The unhydrolyzed phenolsulfonic acid is thereafter subjected to caustic fusion under conditions well known in the art, for example, with sodium hydroxide to prepare the desired dihydroxy- or alkyldihydroxybenzene isomer. The process of caustic fusion as the term is employed herein consists of neutralizing the remaining unhydrolyzed hydroxybenzene- or alkylhydroxybenzenesulfonic acid isomer with an aqueous solution of an alkali metal hydroxide, preferably sodium hydroxide, drying the product, fusing it with caustic, dissolving the fused cake in water and acidifying the fusion reaction product with an acid or acid gases to liberate the desired alkyldihydroxy- or dihydroxybenzene.

Whereas sulfonation of phenol at low temperature produces o- and p-phenolsulfonic acids, and whereas somewhat higher temperatures in the sulfonation will produce p-phenolsulfonic acid in a fairly high degree of purity, still higher temperatures, of 130° and higher and prolonged reaction times are required to produce phenolsulfonic acids having up to a major proportion of the meta-isomer. Inasmuch as phenol that is formed by hydrolysis of the more readily hydrolyzable para and ortho phenolsulfonic acids can of course be recycled to the sulfonation-isomerization step, substantially complete production of resorcinol can be obtained. Resorcinol has many uses in industry, a predominant use being as a component in water and heat resistant resorcinol-formaldehyde adhesives, especially suitable for outside plywood and laminated wood.

The following nonlimiting example is illustrative of a preferred embodiment of the present invention.

A 500 ml three-neck flask, equipped with magnetic stirrer, addition funnel and reflux condenser, was charged with 108.0g (1.0 mole) of m-cresol. Sulfuric acid (96.5%), 147.9g was added dropwise during 25 minutes, while the temperature rose to 80°. External heating by mantle raised the temperature to 107° during 15 min. and Sample 1 was withdrawn. The sample was diluted with water, made basic with aqueous sodium hydroxide and the water was evaporated. The resultant salts, 11.0 g. were fused with 25 g. potassium hydroxide for 40 min. at 235°-330° under a nitrogen atmosphere. The mass was diluted with water, acidified with hydrochloric acid to pH 2 and extracted with four portions of 100 ml each of ether. The solvent was boiled off leaving only 0.5 g. of residue. Infrared and nuclear magnetic resonance showed it to contain 36% m-cresol, 26% diethyl ether solvent and 38% aryl carboxylic acids. There was no evidence of orcinol, methylhydroquinone and methylcatechol. Continuous liquid-liquid extraction of the aqueous phase with ether for five hours only produced 0.2 g. of additional product. A repeat fusion on ca. 25 ml of reaction mixture produced 45 g. of salts which were fused with 100 g. of potassium hydroxide for 35 min. at 350° to 360°. Workup produced only 2.2 g. in which only m-cresol could be identified. The sulfonation resulted in the formation of substantially only m-cresolsulfonic acid isomers wherein the acid group is in ortho and/or para position relative to the hydroxyl group. The failure to obtain methylhydroquinone and/or 4-methylcatechol by fusion from the above m-cresol-sulfonic acids is not surprising in view of Barth and Senhofer's [Ber. 9, 969 (1876)] failure to fuse o- and p- phenolsulfonic acids.

The remainder of the reaction mixture was next isomerized at 173°-178° for 6.5 hours. This was followed by hydrolysis for two hours at 110°-140° in the presence of 33 g. added water. A 25 ml sample of the final product was worked up in the usual fashion. The dried sodium salts amounted to 42.0 g. which were fused with 100 g. potassium hydroxide for 0.5 hr. to 310°. Extraction of the acidified product with ether and evaporation gave 8.4 g. of residue which contained 10% solvent, 54% m-cresol and 36% orcinol (5-methylresorcinol). Substantially pure orcinol can be isolated by any of several means such as distillation, and the m-cresol can be recovered and recycled.

In a similar experiment, with an isomerization temperature of 174°-183°, the final product contained 16.7% m-cresol, 43.1% orcinol and 40.3% α-resorcylic acid (orcinol oxidation product).

While presently preferred embodiments of the invention have been described in particularity, it may otherwise be embodied within the scope of the appended claims.

What is claimed is:
1. A process for the preparation of dihydroxybenzenes wherein the hydroxyl radicals are in meta position to each other, the said process comprising:
   A. heating in the presence of sulfuric acid and at a temperature between 25° and 120° C. a hydroxybenzene having the formula

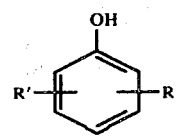

in which R and R' are each selected from the group consisting of hydrogen and an alkyl radical having inclusively from one to four carbon atoms in the alkyl chain, the total number of carbon atoms in radicals R and R' being at most four, thereby forming a mixture of sulfonic acid isomers;
   B. isomerizing the said mixture in the presence of sulfuric acid at a temperature of between 130° and 200° C to obtain an isomeric mixture containing the isomer wherein the sulfonic acid group is meta with respect to the hydroxyl group;
   C. selectively hydrolyzing in an aqueous medium at a temperature between about 100° and 150° C. in the said mixture those sulfonic acid isomers in which the sulfonic acid group is in a position other than meta with respect to the hydroxyl group to produce thereby the selected hydroxybenzene of step A;
   D. caustically fusing the unhydrolyzed meta sulfonic acid remaining in the aqueous medium; and
   E. acidifying the resultant salt of the meta dihydroxybenzene to liberate the desired meta dihydroxybenzene.

2. The process of claim 1 in which the hydroxybenzene is phenol.

3. The process of claim 1 in which the hydroxybenzene is a mixture of cresol isomers including meta-cresol.

4. The process of claim 1 in which the hydroxybenzene is substantially meta-cresol.

5. The process of claim 1 in which the hydroxybenzene is xylenol.

* * * * *

UNITED STATES PATENT AND TRADEMARK OFFICE
CERTIFICATE OF CORRECTION

PATENT NO. : 4,009,212
DATED : February 22, 1977
INVENTOR(S) : Gerd Leston

It is certified that error appears in the above—identified patent and that said Letters Patent are hereby corrected as shown below:

Column 2, line 44, "difficulty" should read --difficultly--.

Column 4, line 3, "110°-140°" should read --110°-130°--.

Signed and Sealed this

Nineteenth Day of April 1977

[SEAL]

*Attest:*

RUTH C. MASON
*Attesting Officer*

C. MARSHALL DANN
*Commissioner of Patents and Trademarks*